United States Patent [19]

Evans

[11] 4,353,370
[45] Oct. 12, 1982

[54] MEDICATED EAR RODS AND EARRING CONSTRUCTION

[76] Inventor: Aida L. Evans, 5706 Irish Hill Dr., Houston, Tex. 77053

[21] Appl. No.: 207,464

[22] Filed: Nov. 17, 1980

Related U.S. Application Data

[63] Continuation of Ser. No. 13,454, Feb. 21, 1979, abandoned.

[51] Int. Cl.³ .............................................. A61M 35/00
[52] U.S. Cl. ..................................... 128/269; 128/330; 63/12
[58] Field of Search ............... 128/260, 269, 270, 271, 128/329 R, 330, 343, 341, 759, 261; 63/12, 13, DIG. 2; 401/128, 129, 130

[56] References Cited

U.S. PATENT DOCUMENTS

| | | | |
|---|---|---|---|
| 511,952 | 1/1894 | Hubash | 63/12 |
| 1,267,067 | 5/1918 | Flagg | 63/14 E X |
| 2,510,490 | 6/1950 | Ager | 128/269 |
| 2,568,207 | 9/1951 | Spicher | 128/329 X |
| 3,500,829 | 3/1970 | Abramowitz | 128/215 |
| 3,527,223 | 9/1970 | Shein | 128/329 R |
| 3,966,558 | 6/1976 | Calva-Pellicer | 128/759 |
| 4,041,946 | 8/1977 | Barton | 128/260 |
| 4,067,341 | 1/1978 | Ivey | 128/330 |
| 4,106,310 | 8/1978 | Abramowitz | 63/12 |

Primary Examiner—Michael H. Thaler
Attorney, Agent, or Firm—Bard, Groves, Sroufe, Ryerson & Jackson

[57] ABSTRACT

A medicated ear rod is provided for cleaning the pierced ear hole of the earlobe. A grooved or ruffled rod member containing an absorbent material loaded with a cleaning agent is adapted to be passed into and out of the earlobe hole and then disposed of. In another embodiment, the ear rod is constructed as part of a permanent earring which can be worn to provide a constant supply of cleaning solution to the earlobe to prevent infection of the ear hole.

1 Claim, 4 Drawing Figures

MEDICATED EAR RODS AND EARRING CONSTRUCTION

This is a continuation, of application Ser. No. 13,454, filed Feb. 21, 1979, now abandoned.

BACKGROUND OF THE INVENTION

This invention relates to an article of manufacture for cleaning the pierced hole of an earlobe. More particularly, the invention relates to a grooved or ruffled rod-like member adapted to contain an absorbent material such as cotton loaded with a cleaning agent to clean the pierced ear hole of the earlobe, to prevent clogging of the earlobe hole and to aid in the healing of an infected pierced ear hole.

One popular item of jewelry has long been the earring. Early earrings included various types of clasps that were attached by compression to both surfaces of the earlobe, but such early type items of jewelry became easily unattached to the lobe with the result that the earring fell off the lobe and was hence lost. Since some earrings had a considerable value, it was sought to find a more permanent method of attaching earrings to the lobe to prevent loss. Also, the above compression-type earrings were often uncomfortable to to the user since they constantly pinched the earlobe. This need brought forth the advent of the pierced ear type of earring where a hole was actually made in the lobe portion of the ear and the earring attached to the lobe by passing a portion thereof through the hole.

While the pierced ear piece solved the problem of loss of valuable items of jewelry it nevertheless introduced the problem of infection in the pierced hole of the lobe and clogging thereof if proper and antiseptic conditions were not always maintained. Since the hole pierced in the lobe is very small, there has not been found on the market any articles of small enough diameter and of particular design to effect cleansing of the pierced hole of the lobe. Crude use has been made of toothpicks for cleaning of the pierced lobe, but toothpicks do not effectively cleanse the hole and are inherently dangerous since wood splinters may pierce the tissue about the pierced hole in the lobe. Metal wires can also be used to clean infected pierced earlobe holes, but these wires likewise are relatively ineffective and unsafe. Most of the antiseptic applicators on the market are not practical for use as earlobe pierced hole cleaners since such applicators are of diameters too large for insertion into the tiny pierced lobe.

Prior art devices also include earrings with hollow rods perforated to allow infectious material to seep into the hollow rod. A cleaning tool may then used to push the infectious material from the interior of the rod, and medicament can be caused to flow into the hollow rod and thence through the perforations to the earlobe. Such devices are obviously complicated and have limited practical value.

These disadvantages and insufficiencies are overcome with the present invention wherein improved articles of manufacture are provided which are particularly designed to clean out the pierced ear hole of the earlobe, to prevent the clogging of the pierced hole, to maintain the ear hole open and receptive when the earring is not being worn, and to function as an applicator to aid in the healing of an infected pierced ear hole. Further, the articles of manufacture of the herein described invention may be constructed to be disposable after use, and are made of materials which render the article relatively inexpensive.

SUMMARY OF THE INVENTION

This invention relates to apparatus for cleaning pierced holes in ear lobes. The apparatus includes a disposable solid plastic rod with a coarse peripheral surface adapted to aid in removing infectious material from the tissue about the pierced hole, and a handle for easy manipulation of the rod. The plastic rod may contain an absorbent gauze pad to retain a medicament to inhibit further infection and aid the healing of the infected tissue. If the rod is to be worn by the user, the handle may be constructed to cover the infected tissue, and a rod clasp containing medicament used in conjunction with the rod.

In another embodiment, an ear rod is provided which contains grooves or ruffles in the surface thereof and which surfaces function to trap therein leukocytes, tissue debris, and dry and flaky skin that may be accumulated within the pierced hole of the lobe. Thus, the ear rod functions in the fashion of a reamer wherein the grooves or ruffles in the surface of the ear rod gently scrape unwanted debris from the opening in the lobe.

In one preferred form, an absorbent material such as cotton is wrapped about the ear rod and preferably within the confines of the grooves or ruffles. After a cleaning agent such as hydrogen peroxide or alcohol is applied to the cotton, the ear rod may be passed into and out of the earlobe opening for the purpose of applying an antiseptic medicament to the lobe hole to heal or prevent build-up of infection therein. The ear rod may also include at least one upstanding barb thereon to remove otherwise stubborn deposits lodged with the earlobe hole. For gentler applications, the ear rod may be provided with a reduced diameter portion extending midway of the rod length and a layer of gauze or cotton applied thereto for the purpose of holding the cleaning or antiseptic agent or agents.

In another preferred embodiment of the herein set forth novel article of manufacture, the ear rod may be adapted to function as the ear pole piece of an otherwise useable earring. Thus, the above described ear rods may include a stopper member attachable to the free end of the rod to attach the rod to the lobe after the rod has been inserted in the pierced ear hole of the lobe. The stopper may be packed with cotton whereby an antiseptic agent absorbed in the cotton filled stopper will provide a source of cleaning agent that will move from the stopper and along the rod section of the article and into the interior of the pierced opening in the lobe. In this form, a constant supply of cleaning agent will be fed to the ear opening for the maintenance of antiseptic conditions therein.

It is therefore a feature of the present invention to provide a disposable and hand manipulatable ear rod constructed of a plastic material and at least partially containing an absorbent cottom or gauze for carrying a cleaning agent.

It is another feature of the present invention to provide an ear rod of constant diameter, so that the rod can be easily inserted into the opening in the earlobe.

It is also a feature of the present invention to provide a grooved or ruffled or otherwise uneven surface area on the ear rod for reaming and trapping debris located in the opening in the earlobe.

It is a further feature of the present invention to provide a permanent earring construction including a grooved or ruffled ear rod pole piece containing an absorbent substance and a cooperating ear stopper filled with cotton and containing an antiseptic agent, and with the ear stopper being so constructed and arranged so as to be received on the free end of the ear rod pole piece for attachment of the earring to the lobe of the user.

It is also a feature of the present invention to provide a cleaning device for use in a pierced earlobe and the like, comprising an elongate rod-like member having a reaming portion for insertion into and at least partially through said pierced earlobe and further having a free end and a handle means at the other end of said reaming portion, and said reaming portion being substantially rigid and further having spaced-apart groove means along the length thereof.

There and other features and advantages of the present invention will become apparent from the following detailed description wherein reference is made to the figures in the accompanying drawings.

DRAWINGS

DETAILED DESCRIPTION

Figure 1:
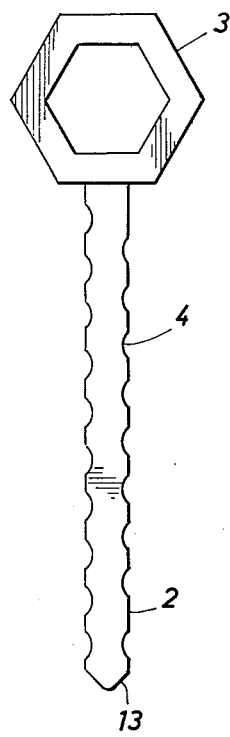
FIG. 1 is a simplified pictorial representation of one form of the ear rod of the present invention.

Referring now to FIG. 1, there may be seen a simplified pictorial representation of one form of ear rod member of the present invention and comprising an elongated solid rod 2 which is preferably of a cross-sectional size approximating that of the pierced hole of an earlobe. Rod 2 may be constructed of a plastic material such as polyethylene, Teflon, or in some cases a polyurethane composition may be employed. In any event, a plastic is preferred since many people suffer allergic reactions to metal, and splintering problems are not encountered as in the case of wooden rods.

Integrally formed at one end of the rod 2 is a handle element 3 shown in the fashion of a hexagon, although other shapes and designs may be provided such as square, triangular, rectangular, or even decorative designs as star-shaped or flowered. It is desirable that handle 3 provides a means of grasping whereby the rod portion 2 may be alternately inserted and withdrawn from the pierced opening of the earlobe.

The surface of the rod 2 is preferably shaped other than smooth and continuous and is seen to include a plurality of grooves 4 along the length thereof. Shapes other than grooves 4 may be provided such as ruffled or even serpentine like, the only provision being that some form of trap be found in the surface of rod 4. The grooves 4 may be aligned with the length of the rod 2, although the embodiment shown in FIG. 1 is preferred. The grooves 4 form a serrated surface for rod 2 wherein insertion of rod 2 into and out of the pierced hole of the earlobe will ream the hole. Thus, grooves 4 ream the ear hole and remove therefrom pus, dry and flaky skin or tissue that may be accumulated therein. This reaming action of grooves 4 tends to clean the opening and otherwise unclog the opening and free it for access of the earring when attached. Although the surface of rod 2 is described in terms of recesses in the rod or grooves, it is apparent that the same result may be achieved by adding ridges to an otherwise smooth rod, and such is certainly within the concept of the present invention.

Rod 2 may have a uniform diameter along its length, so that the rod 2 can be easily inserted in the earlobe and the full length of the rod 2 may be used to clean the hole. Handle member 4 may also be constructed of plastic as is the case for the rod element 2. The ear rod of FIG. 1 can be inexpensively manufactured by conventional injection molding techniques, for example.

In order to function as a cleaning tool in a reaming manner, rod 2 is preferably rigid in construction, although, as previously stated, it may be constructed of plastic. Since rod 2 is thin, it will bend slightly when used, however the rod 2 may be more closely analogized to a rigid rod than to a limp rod.

The cross-sectional configuration of rod 2 may vary according to the instant invention, although an elliptical configuration is preferred. The mean diameter of rod 2 will generally be greater than 0.010 inches and generally less than 0.075 inches, and the preferred mean diameter is generally in the range of 0.020 to 0.040 inches.

In use, handle 3 of the ear rod of FIG. 1 is grasped between the thumb and forefinger and the free end 13 is inserted into the pierced opening of the earlobe. It is then simply required to continue to alternately move the grooved portion 4 of the rod 2 in and out through the pierced lobe opening to scrape away therefrom leukocytes, tissue debris or dry skin therein. If desired, rod 2 may be may be constructed with a slight taper away from the handle member 3, so that the user could apply the desired amount of pressure to the ear hole. These materials deposit in the grooves 4 and the ear rod 2 may thereafter be disposed of after a single use.

It may be desirable in some instances of use of the ear rod of FIG. 1 to dip the rod into a cleaning agent prior to use to coat the exterior surface of the rod. Also, if retained in a cleaning agent for a sufficient time, the ear rod 2 may absorb some of the cleaning agent. Thus, hydrogen peroxide or alcohol may be applied to the ear rod, and then the ear rod used as above described. This has the advantage that a medicant can be applied to the pierced ear hole concurrently with the removal of debris therefrom. The medicant will coat the pierced hole and act to assist in the healing of any infection therein or at least to prevent further infection.

Figure 2:
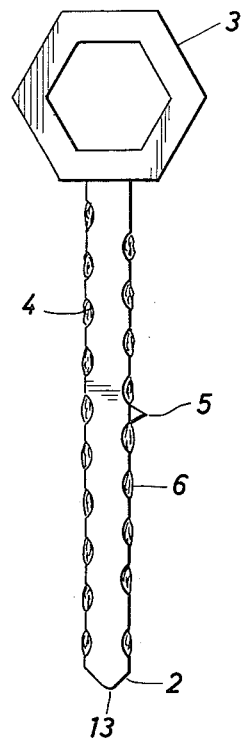
FIG. 2 is a simplified pictorial representation of another form of the ear rod of the present invention.

With reference now to FIG. 2, there is shown a simplified pictorial representation of a second embodiment of the invention similar in construction to FIG. 1 but including further perfecting features. Like numerals will be seen to indicate like parts.

In this embodiment of FIG. 2, there will be seen rod 2 and handle 3 of plastic construction preferably solid, and including grooves or ruffles 4. An absorbent material 6 of either cotton or gauze is interlaced into the grooves 4 and functions as a more positive carrier for cleaning agent. Thus, prior to use, the ear rod of FIG. 2 may be dipped into alcohol or hydrogen peroxide whereby this cleaning agent will be taken up by the adsorbent cotton area 5 for application to the pierced hole of the lobe as previously described. In the case of stubborn encrustations of debris within the lobe, a barb 5 may be formed on the rod portion 2 for removing debris from the earlobe opening. Application of alcohol, hydrogen peroxide or other cleaning fluid to the rod not only tends to sterilize the ear rod before use but also loads the absorbent areas 6 with cleaning agent for application to the lobe hole.

Figure 3:
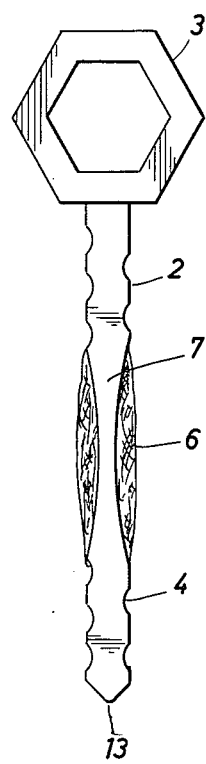
FIG. 3 is another simplified pictorial representation of yet a further embodiment of the ear rod of the present invention.

Another embodiment of the invention is set forth pictorially in FIG. 3 and again like parts are shown by like numerals. As seen in FIG. 3, the ear rod has integrally formed thereto serrated or grooved section 2 interrupted by a contoured section 7 of diminishing cross-sectional shape. Section 7 of rod 2 provides an area where either an absorbent plastic, cotton or gauze may be wrapped and adapted to be coated with the cleaning agent. In this embodiment, the grooved surface area is maintained and an increased area for cleaning solution absorbency is provided. In any event, the ends of the rod adjacent handle 3 and free end 13 may still include grooved areas 4 to scrape debris from the lobe opening and a large and continuous applicator section 6 of cotton or gauze containing alcohol, hydrogen peroxide or other appropriate and conventional antiseptic agents. In other respects, the embodiment of FIG. 3 is used in a fashion similar to that set forth above with respect to FIGS. 1 and 2.

Figure 4:
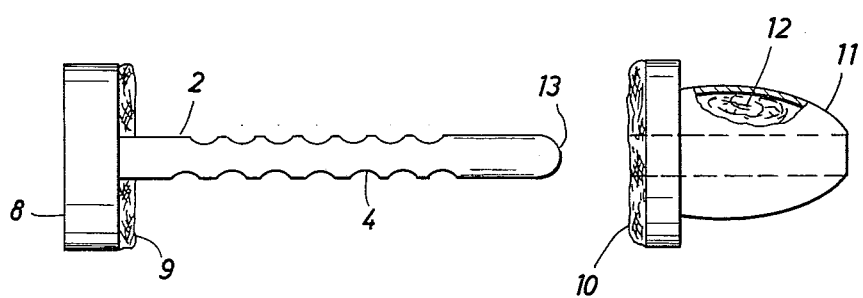
FIG. 4 is a simplified pictorial representation of an earring construction employing the ear rod of the present invention.

In many cases, infection may be so severe that some type of permanent antiseptic applicator will be called for which will not only function as an earring for aesthetic purposes but also provides a means of discharging cleaning agent to the area of the earlobe opening. For this purpose, an earring is provided and as seen in FIG. 4 includes a rigid ear pole pierce 8 that may include on its surface some exposed earring design.

Pole piece 8 has extending therefrom a rigid ear rod 2 terminating in free end 13. Again grooves or ruffles 4 may be provided on ear rod 2 and these grooves 4 may have interlaced therein cotton or gauze as seen in the embodiment of FIGS. 2 and 3.

Free end 13 is inserted through the pierced ear hole and pole piece 8 rests against the visible surface of the lobe. A section of gauze 9 may be included on the inner side of piece 8 for antiseptic purposes. The pole piece 8 may be of such a size that it will cover the infected tissue while the earring is being worn.

Stopper member 11 is provided to be received over the free end 13 of ear rod 2 in order to attach the assembly to the ear. Varius methods may be employed for attaching the stopper member 11 to the ear rod 2. For instance, rod 2 may contain a recess (not depicted) near the free end 13 which is designed to snap into a portion of the stopper member 11. Also, the passageway through the stopper member 11 may be sized so that friction between the ear rod 2 and the stopper member 11 will keep these parts attached. Further, the stopper member 11 and the pole piece 8 may be permanently joined by a flexible member (not depicted) which may prevent the inadvertent loss of one portion of the earring.

Again for antiseptic reasons, a gauze layer 10 may flank stopper 11. Stopper 11 may be open at only the gauze end or at both ends, and may be filled with cotton in the interior thereof. Alcohol or hydrogen peroxide may be poured into stopper 11 until the cotton 12 therein and the gauze 10 are saturated. If desired, the ends of the stopper 11 may thereafter be temporarily sealed, e.g. with a thin plastic wrap, and the seal broken when the earring is to be used. This embodiment will provide a continuous supply of cleaning agent to the rod 2 as the earring of FIG. 4 is worn. Thus, cleaning agent will ooze out of stopper 11 and onto rod 2 which will in turn antiseptically treat the pierced ear opening. Eventual oozing of cleaning agent may soak gauze pad 9 whereby all surface areas adjacent the lobe opening will contain cleaning agent to prevent infection or to cure any existing infection. It is noted that the other ear rod designs as set forth in FIGS. 1–3 are applicable and can be adapted for use in the earring embodiment of FIG. 4. In the case of FIG. 2, the barb 5 would be eliminated. In other respects, the materials of construction of the earring of FIG. 4 may be of plastic as noted above with the possible exception of the pole piece which could be jeweled or ornamentally fashioned.

Many other alternative forms of the present invention will, of course, become apparent from the foregoing. Although the invention herein has been depicted for use in the hole of an earlobe, it is apparent that the invention may also be employed for the same purposes to clean the pierced hole in other areas, such as the nose. Accordingly, the structures hereinbefore depicted and discussed are illustrative only, and are not intended as limitations on the scope of the present invention.

What I claim is:

1. A medicated earring comprising:
    a substantially rigid elongate plastic member having a filled interior for insertion through a pierced earlobe;
    an enlarged pole piece attached to one end of said elongate member for abutting and covering one side of said pierced earlobe;
    stopper means adapted to be removably secured to the other end of said elongate member for retaining said plastic member within said pierced earlobe; and
    an absorbent material carried by said stopper means and adapted for engagement with a portion of said plastic member and for receiving a cleaning agent, wherein a portion of said elongate member has a substantially reduced diameter, and additional absorbent material is located adjacent said reduced diameter portion.

* * * * *